US006847190B2

(12) United States Patent
Schaefer et al.

(10) Patent No.: US 6,847,190 B2
(45) Date of Patent: Jan. 25, 2005

(54) METHOD AND APPARATUS FOR CHARGING STERILIZABLE RECHARGEABLE BATTERIES

(75) Inventors: Martin A. Schaefer, Clearwater, FL (US); Ronald R. Reinhart, St. Petersburg, FL (US)

(73) Assignee: Linvatec Corporation, Largo, FL (US)

( * ) Notice: Subject to any disclaimer, the term of this patent is extended or adjusted under 35 U.S.C. 154(b) by 35 days.

(21) Appl. No.: 10/374,579

(22) Filed: Feb. 25, 2003

(65) Prior Publication Data

US 2003/0160590 A1 Aug. 28, 2003

Related U.S. Application Data

(60) Provisional application No. 60/359,463, filed on Feb. 26, 2002.

(51) Int. Cl.[7] .......................... H01M 10/44; H01M 10/46
(52) U.S. Cl. ....................................................... 320/107
(58) Field of Search ................................ 320/107, 110, 320/112, 114; 429/96, 97, 98, 99, 100

(56) References Cited

U.S. PATENT DOCUMENTS

| | | | | | |
|---|---|---|---|---|---|
| 4,288,733 A | * | 9/1981 | Bilanceri et al. | ........... | 320/113 |
| 4,302,714 A | * | 11/1981 | Yefsky | ........... | 320/131 |
| 4,609,860 A | * | 9/1986 | Fasen | ........... | 320/131 |
| 4,641,076 A | * | 2/1987 | Linden | ........... | 320/113 |
| 4,641,077 A | * | 2/1987 | Pascaloff | ........... | 320/113 |
| 5,334,925 A | * | 8/1994 | Kendrick | ........... | 320/131 |
| 6,018,227 A | * | 1/2000 | Kumar et al. | ........... | 320/106 |
| 6,181,105 B1 | * | 1/2001 | Cutolo et al. | ........... | 320/115 |

\* cited by examiner

*Primary Examiner*—Edward H. Tso
(74) *Attorney, Agent, or Firm*—Gene Warzecha

(57) ABSTRACT

A method and apparatus for charging rechargeable batteries for use in a sterile field with powered surgical instruments. The method comprises the steps of placing the batteries in a sterilization/charging container, discharging the batteries to a predetermined level and then sterilizing, charging and storing them without removing them from the container until they are needed. The charged batteries may be removed directly into the sterile field.

32 Claims, 6 Drawing Sheets

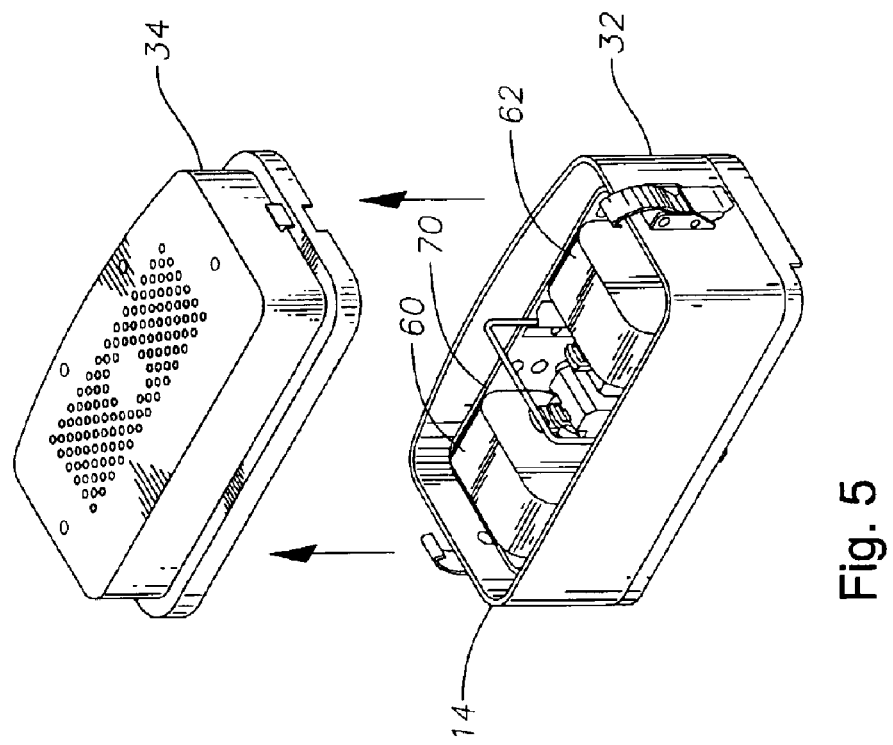
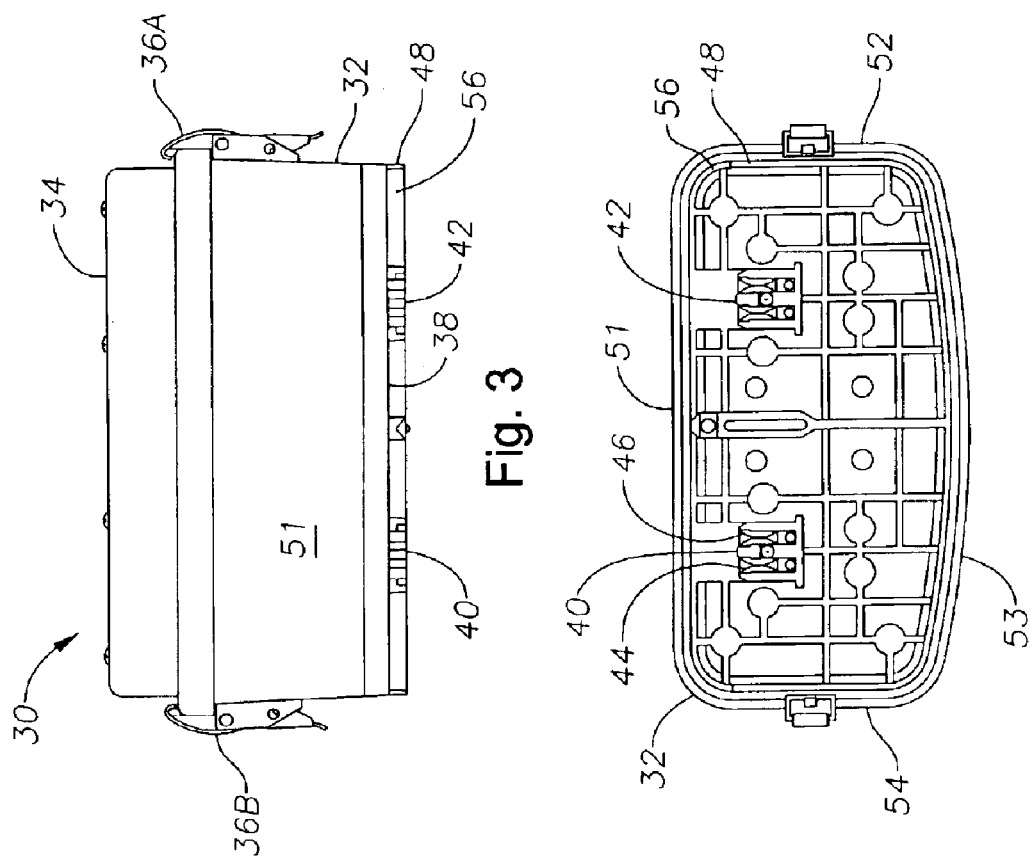

METHOD AND APPARATUS FOR CHARGING STERILIZABLE RECHARGEABLE BATTERIES

RELATED APPLICATIONS

This application claims the benefit of U.S. Provisional Application No. 60/359,463, filed Feb. 26, 2002.

BACKGROUND OF THE INVENTION

1. Field of the Invention

The invention relates to powered surgical devices. More particularly, the invention relates to rechargeable batteries used in powered surgical devices. Still more particularly, the invention relates to methods and apparatus used to sterilize and charge batteries used in powered surgical devices.

2. Description of the Prior Art

The use of rechargeable batteries in powered surgical devices used in the sterile surgical field is well known. After each use the batteries must be charged and sterilized, preferably by autoclaving. It is known that if the batteries are charged before being autoclaved they lose a significant portion of the charge and their useful life due to the heat of the sterilization process. If the batteries are charged after being autoclaved, the sterility is compromised by exposure to the battery charger. A solution to this problem has been identified in U.S. Pat. No. 4,641,076 (Linden), Method and Apparatus for Sterilizing and Charging Batteries, assigned to the assignee hereof and incorporated by reference herein.

While the invention disclosed in the aforementioned Linden patent is advantageous in that it provides a sterilization/charging container which enables a battery to be sterilized within the container and then charged within the container while in a sterile state, the invention relates to improvements which have been discovered to increase the useful life of rechargeable, sterilizable batteries.

As mentioned, it is known that batteries, when subjected to the heat of the autoclaving process, ultimately have shorter useful lives. The battery cells are generally nickel-cadmium (Ni—Cd) and as the batteries are heated in an autoclave for a long time they reach a point where the temperature in the autoclave causes the battery's temperature to increase even further. This is due to the known self-discharge rate characteristic of Ni—Cd batteries. The rate is 1% per day at room temperature and doubles for every 10 degrees above room temperature. It is clear that at autoclave temperature, generally 270–272° F. (132–133° C.), the self-discharge rate is very high. The increasing battery temperature causes the battery to self-discharge more, again increasing the battery temperature and the cycle continues until the battery temperature is even greater than the autoclave temperature. Such thermal runaway creates the high temperatures which destroy the battery cells and cause the battery to be unable to accept a full charge in subsequent uses.

This phenomenon has been addressed in some instances by using shorter autoclave cycles to avoid reaching the point of runaway battery temperature. However, some in the medical field view this as a solution which compromises the sterility of the battery. Those with this view must either accept battery powered handpieces with relatively short battery lives or must use non-battery powered devices. Given the advantages of battery powered devices it would be desirable to produce a battery system which avoids the shortcomings of prior art battery sterilization/charging systems.

In addition to increasing the useful life of rechargeable batteries, the invention relates to improvements in operating a sterilizing/charging system such as that shown in the aforementioned Linden U.S. Pat. No. 4,641,076.

Accordingly, it is an object of this invention to provide a system for storing and charging batteries for surgical powered instruments.

It is also an object of this invention to provide a system which enables one or more batteries to be retained in a sterilization/charging container in which the batteries may be sterilized and then charged while in a sterile state.

It is another object of this invention to provide a system for charging sterilized batteries while optimizing the useful life of autoclaved batteries.

It is also an object of this invention to provide a system by which the mateable engagement of a sterilization/charging container containing rechargeable batteries and a charger is facilitated.

SUMMARY OF THE INVENTION

These and other objects of this invention are achieved by the preferred embodiment disclosed herein. In one aspect, the invention comprises a method for sterilizing a battery comprising the steps of placing the battery in a sealable sterilization/charging container which permits sterilization media to penetrate the container but does not permit contaminants to penetrate; discharging the battery to a first predetermined voltage level without removing it from the container; sterilizing the battery without removing it from the container; charging the battery without removing it from the container to a second predetermined voltage level; and storing the battery in a sterile state without removing it from the container.

In another aspect, the invention comprises a battery charging system for charging a battery to be sterilized. The system comprises a sterilization/charging container for containing and maintaining a sterile battery, the container comprising a peripheral wall and conductive terminal means extending through the wall. The system also comprises a battery charger/discharger for selectively discharging and charging the battery in the container. The battery charger comprises at least one battery receiving station for receiving the container, the station provided with electrical terminals for receiving the terminals of the sterilization/charging container. A discharge circuit means is associated with the battery receiving station for determining if the level of voltage from a battery in the container at the charging station is above a predetermined level and, if so, for depleting energy in the battery to a predetermined voltage level. The system also comprises interrupting means for stopping the depletion of energy from the battery when the predetermined voltage level has been reached, thereby enabling the sterilization/charging container with the charge-depleted battery therein to be removed from the battery charger and charged. The system also comprises charging means associated with the battery receiving station for charging the battery within the container after it has been removed from the receiving station, sterilized and returned to the receiving station.

BRIEF DESCRIPTION OF THE DRAWINGS

FIG. 3 is a front elevational view of the container shown in FIG. 2.

FIG. 4 is a bottom plan view of FIG. 3.

FIG. 5 is a front perspective view of the sterilization/charging battery container of FIG. 2 showing the cover being removed.

DESCRIPTION OF THE PREFERRED EMBODIMENT

It has been discovered that discharging a rechargeable battery prior to autoclaving is a way to prevent runaway battery temperatures. Discharging a rechargeable battery prior to charging is known as "conditioning" and is a step known to minimize the "memory" effect of such batteries. Some non-medical battery chargers have "conditioners" built in. However, it has been discovered that such conditioning decreases the energy stored in a battery to a point which prevents thermal runaway so that autoclaving for a relatively long time has little or no detrimental effect on the battery. Using the teachings of the aforementioned Linden U.S. Pat. No. 4,641,076 to encase a battery prior to sterilization, the inventors have developed a sterilization/charging system which dramatically increases the useful life of autoclaved batteries. As used herein, "useful life" means the number of autoclave sterilization/charging cycles to which a rechargeable battery may be subjected while still enabling the battery to be charged sufficiently to satisfactorily operate a powered surgical instrument.

Figure 1:
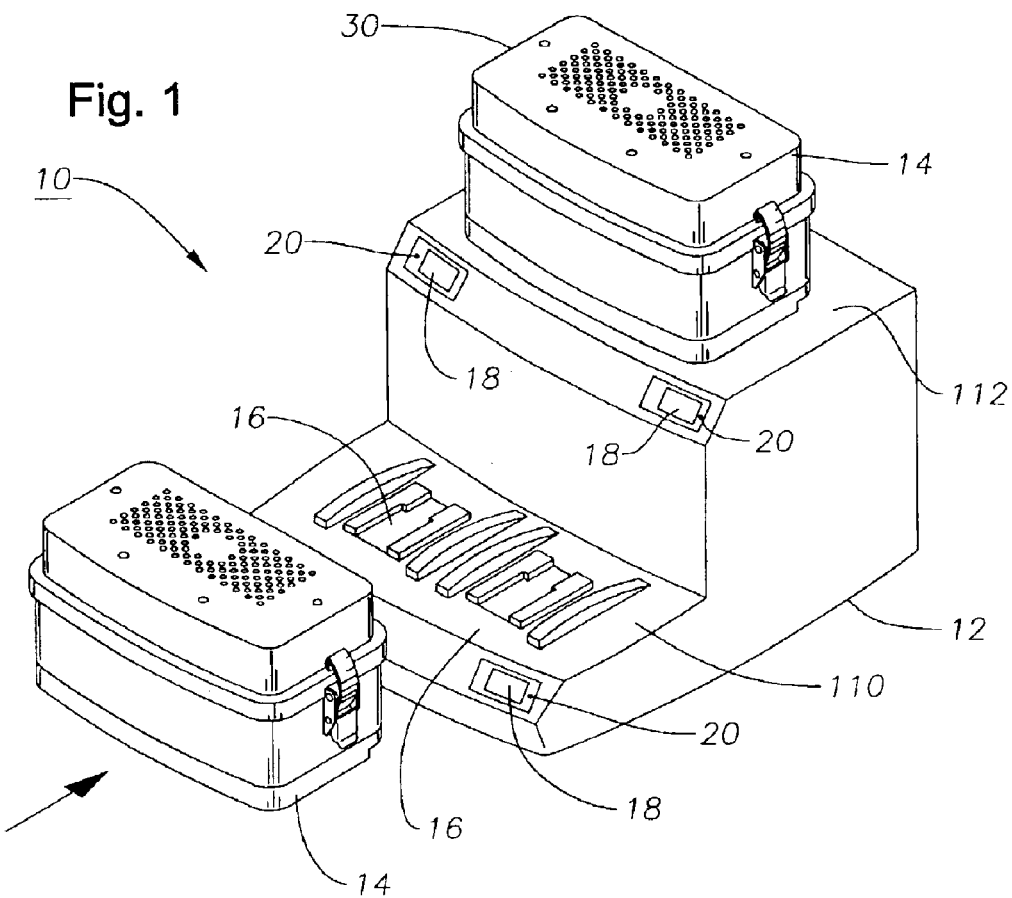
FIG. 1 is a front perspective view of a battery charging system constructed in accordance with the principles of this invention.

As shown in FIG. 1, a sterilization/charging system 10 constructed in accordance with the principles of this invention comprises a battery charger 12 and one or more battery-containing sterilization/charging containers 14. Battery charger 12 comprises a plurality of battery charging stations 16 each of which is provided with a pair of electrical terminals (positive and negative) for mating engagement with the terminals of an individual battery. Battery charger 12 also comprises an on/off switch 18 and a ready-light indicator 20 associated with each charging station 16. In the preferred embodiment, battery charger 12 is designed to have its battery charging stations 16 arranged in pairs in a lower tier 110 and an upper tier 112, each tier adapted to slidably receive a sterilization/charging container 14.

An individual sterilization/charging container 14 is shown in FIGS. 2 through 9. Container 14 comprises a body 32 and a removable cover 34, body 32 and cover 34 attached together by latches 36A and B. Container 14 further comprises a pair of charging terminal sets 40 and 42 situated on the bottom surface 38 of body 32. Each terminal set comprises a pair of spring loaded electrical contacts 44 and 46, each pair 44, 46 comprising opposed leaf springs adapted to slidably receive an electrical blade contact situated at the charging stations 16 on battery charger 12. In the preferred embodiment, sterilization/charging container 14 is adapted to charge two batteries simultaneously and, therefore, is provided with a terminal set 40/42 for each battery. It will be understood that the invention will operate equally well with a sterilization/charging container adapted to hold any number of batteries.

Figure 2:
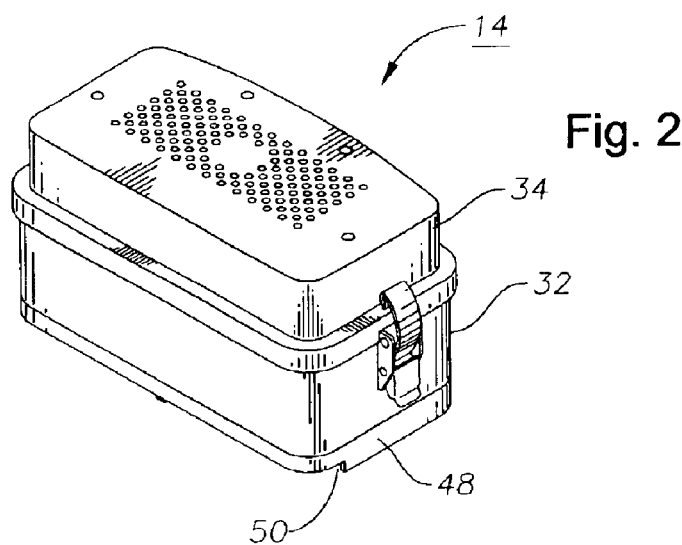
FIG. 2 is a front perspective view of the sterilization/charging battery container used in the system shown in FIG. 1.
Figure 6:
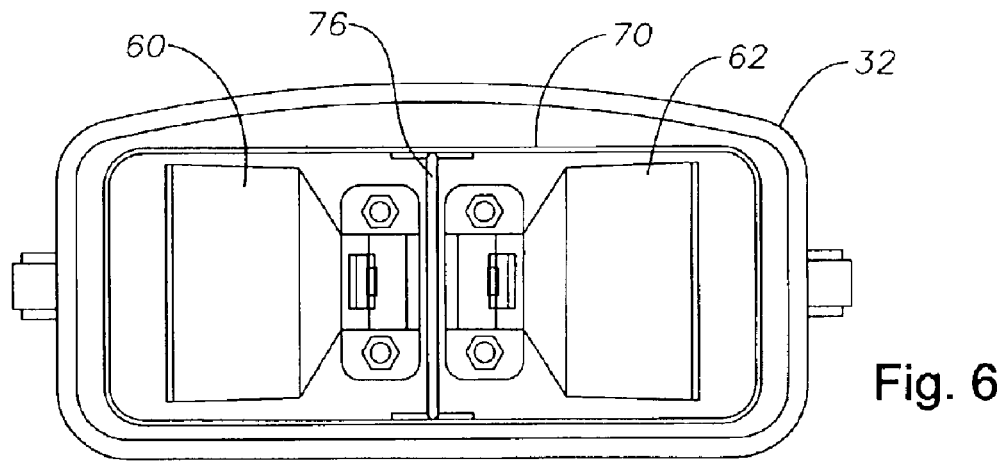
FIG. 6 is a top plan view of the container of FIG. 5 with the batteries in place but with the cover removed.
Figure 7:
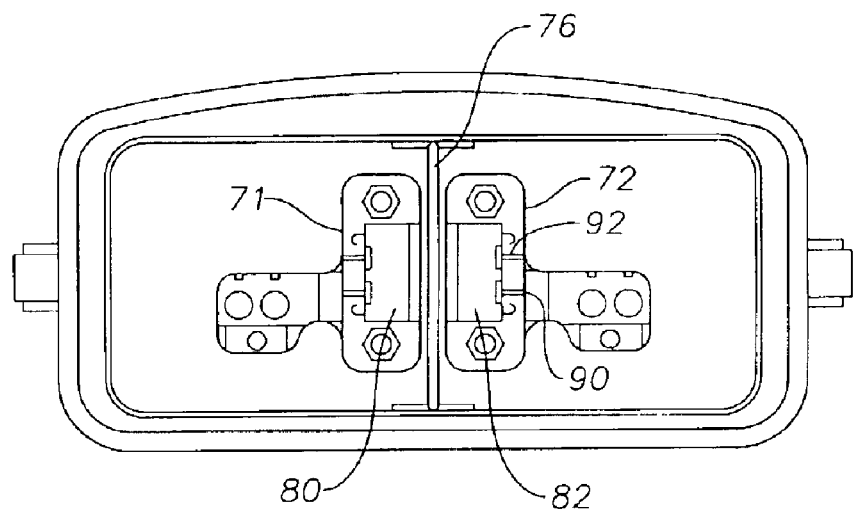
FIG. 7 is a view of FIG. 6 showing the container with the batteries removed.
Figure 8:
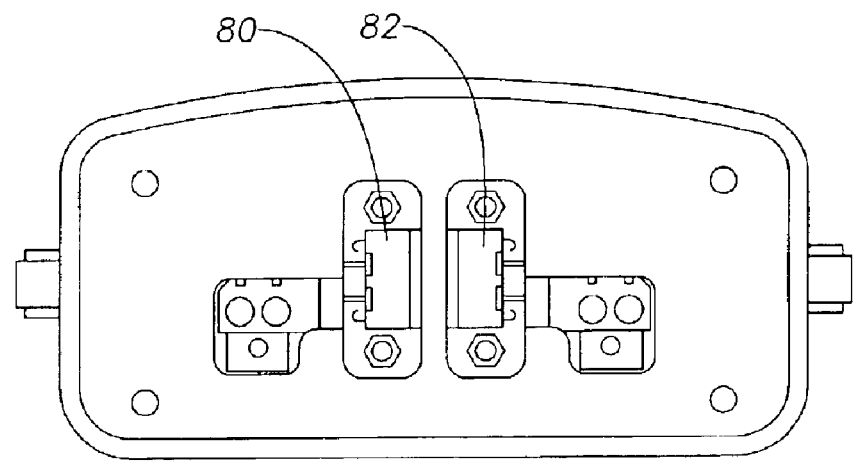
FIG. 8 is a view of FIG. 7 with the basket removed.
Figure 9:
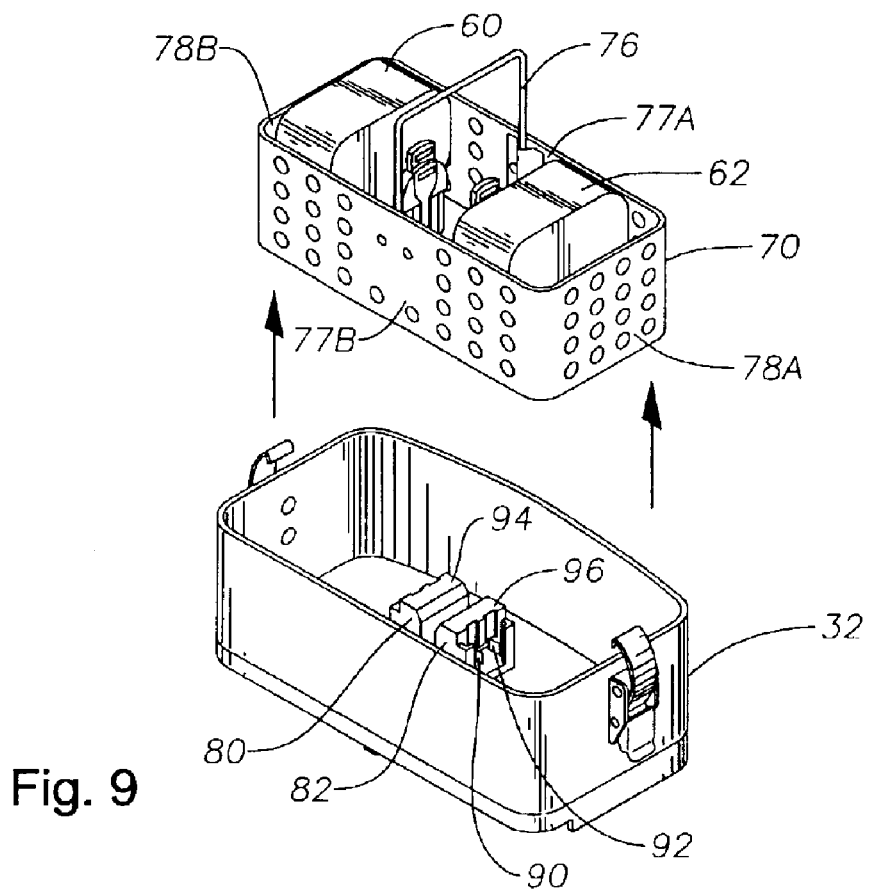
FIG. 9 shows the container of FIG. 5 and the manner in which batteries and a battery tray may be removed.
Figure 10:
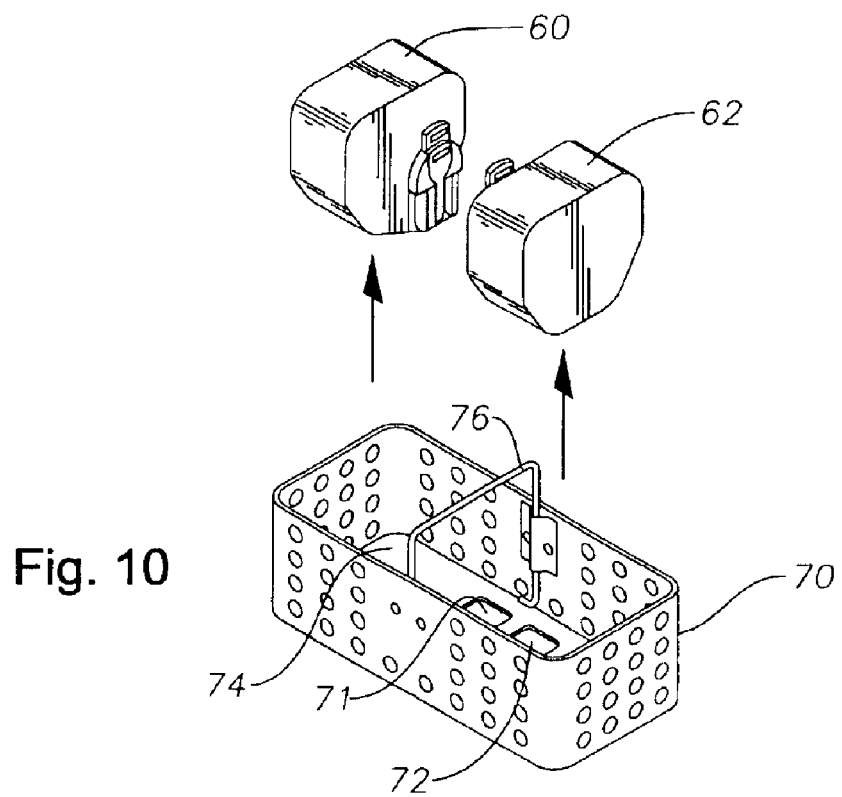
FIG. 10 shows the manner in which batteries may be removed from the basket shown in FIG. 9.

As best seen in FIGS. 2 and 3, container 14 is, when sealed, provided with a peripheral wall 48 extending entirely around the interior 50 of the container 14. It will be understood that peripheral wall 48 comprises four side walls 51, 52, 53, 54, bottom wall 38 and cover 34. Side wall 51 is recessed at 56 in order to enable it to support container 14 on a flat surface while protecting contacts 44 and 46 and enabling container 14 to horizontally slide onto the battery charging stations 16 of charger 12 to effect slidable engagement of electrical contacts 44 and 46 with their respective contacts on the charger. The slidable contacts enable the container to be removed vertically or horizontally. It will be understood that the various mating contacts could be in many other forms including, for example, plug and socket combinations enabling vertical engagement and disengagement.

As shown in FIG. 5, cover 34 may simply be lifted off body 32 to allow access to batteries 60 and 62 situated within container 14. Cover 34 may equally well be hinged or otherwise connected to body 32. It will be understood that each battery 60, 62 may comprise a plurality of individual cells. Consequently, batteries 60, 62 are sometimes referred to as battery packs. The term "battery" as used herein is intended to refer to individual batteries and battery packs.

As best seen in FIGS. 5 through 10, batteries 60 and 62 are situated within a perforated sterilization/charging basket 70 which is itself situated within body 32. Sterilization/charging basket 70 has perforated side walls 77A and B and 78A and B and is provided with a handle 76 and a pair of access apertures 71 and 72 in its bottom surface 74. Sterilization/charging basket 70 is thus able to be placed within body 32 around electrical contact sets 80 and 82. Handle 76 facilitates removal of the basket and sterilized batteries without compromising battery sterility. Each electrical contact set 80 and 82 comprises a pair of terminals 90 and 92 in the form of linear blades. Each set 80 and 82 further comprises a stand or battery holder 94 and 96, respectively, for mateably engaging a battery in order to hold it firmly to enable good electrical contact between the battery terminals and terminals 90 and 92. It will be understood that interior terminal sets 80 and 82 are electrically connected to exterior terminal sets 40 and 42, respectively.

Because batteries are placed in sterilization/charging container 14 in a non-sterile state, the preferred method of loading batteries into container 14 is to first place basket 70 into body 32 thereby leaving terminal sets 80 and 82 accessible above the bottom surface 74 of tray 70. Batteries 60 and 62 may then be mateably joined with terminal sets 80 and 82 and then the container 14 may be sealed by latching cover 34 to body 32.

Figure 11:
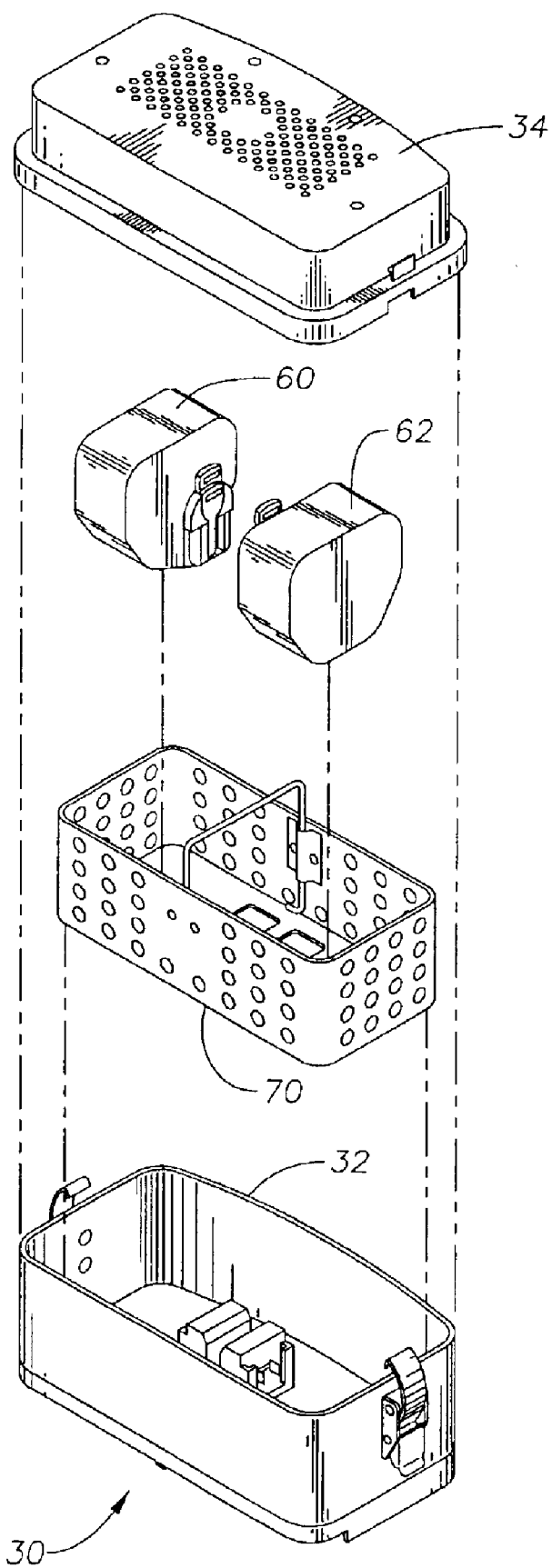
FIG. 11 shows the sterilization/charging container of FIG. 2 in a front perspective, expanded view showing the relationship between various components.

FIG. 11 shows the manner in which the various components of a loaded sterilization/charging container 14 may be assembled.

Figure 12:
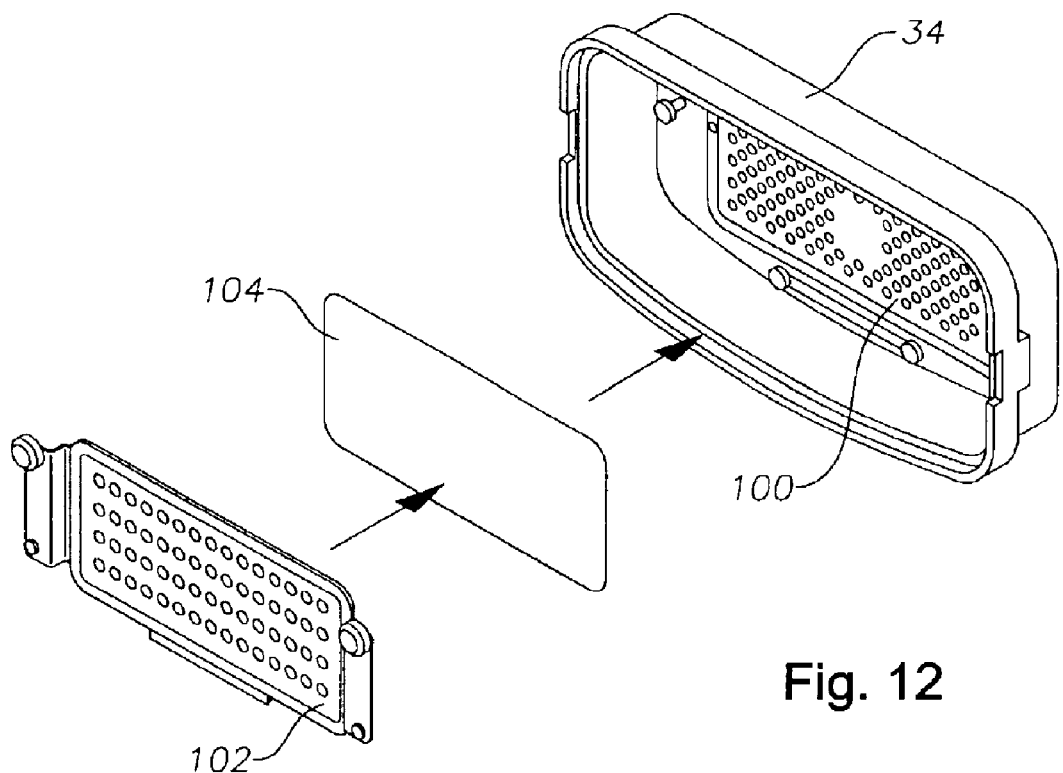
FIG. 12 shows a bottom perspective view of the lid portion of the sterilization container shown in FIG. 5.

FIG. 12 shows that cover 34 comprises a plurality of apertures 100 extending through its top surface, an apertured plate 102 adapted to be secured adjacent apertures 100 on the inside of the cover 34 and a semi-permeable membrane 104 adapted to be retained between the apertures 100 and apertured plate 102. It will be understood that membrane 104 is permeable to steam, heat and other sterilizing media that may be utilized to sterilize batteries within the sterilization/charging container while it is impermeable to contaminants. The terms "sterilizing media" and "sterilizing medium" as used herein may include an autoclave or any other sterilizing means. Membrane 104 is preferably disposable after each use.

The use of the above described apparatus will now be described in conjunction with the method disclosed herein. Discharging a rechargeable battery prior to autoclaving has been found to enhance the number of usage cycles for which the battery may be used. The invention, therefore, enables optimization of the useful life of sterilized batteries by providing a way to discharge a battery before it is sterilized without jeopardizing the sterility of the battery after autoclaving. That is, as will be understood below, a battery to be sterilized and charged may first be sealed within the sterilization/charging container 14, then discharged while in the container, then sterilized while in the container and, finally, charged while in the container.

The method of using the invention is shown in FIGS. 5 through 11. After use, a battery will be removed from its handpiece (not shown) and cleaned prior to sterilization and charging. Basket 70 is placed into container body 32 (FIG. 9), leaving electrical contact sets 80 and 82 accessible, and then one or more batteries are inserted into the basket by sliding the battery terminals onto the terminals 90, 92 of the respective contact set. The cover 34 is latched on to the body 32 loaded with batteries. In order to pre-condition the battery for optimal charging, the battery must first be discharged before being subjected to the heat of autoclaving. Accordingly, the loaded sterilization/charging container 14 is first slidably placed on a selected tier of charger 12 so that the contacts 44, 46 of terminal sets 40 and 42 are mateably engaged with complementary contacts in each charging station 16. The engagement of contacts on the charger and the container is direct, without the use of any intermediate cable or other connectors. In the preferred embodiment, since some users may not want to maximize battery useful life and may prefer simply to charge a battery, charger 12 may be provided with alternate controls and associated circuits. The circuits are not described in detail because those skilled in the art will understand these circuits by the functions described below. Thus, a user may activate a "charge" button, an "automatic discharge/charge" button or a "manual discharge/charge" button. A "charge" button could be used to automatically charge the battery using a predetermined charging current profile. Alternatively, charging could begin automatically upon engagement of a battery with the terminals at charging station 16. An "automatic discharge/charge" button could be used to automatically sense the battery and information (e.g. number of cells, etc.) embedded in a chip in the battery and determine if it is necessary to discharge the battery to a predetermined level, and then automatically charge it to a new predetermined charge level. In the preferred embodiment the discharge level is approximately 0.9 volt per cell and the charge level is minimal. A "manual discharge/charge" button could be used to automatically discharge the battery to the aforementioned predetermined discharge level and then stop to allow the battery to be sterilized and then returned to the charger. Once so returned, the user may simply activate either "automatic" button to have the battery charged to the predetermined charge level.

In the preferred embodiment, charger 12 is automatically programmed to begin the charging cycle one minute after a battery is positioned at station 16 unless an on/off button 18 is activated within a minute. This stops the charging process with the charge optimally depleted from the battery so that the sterilization/charging container 14 may then be removed from charger 12 and autoclaved. After sterilization, the batteries may be charged while still in the same sterilization/charging container. To the extent that battery charger 12 may have a discharge circuit built in, the charger may be referred to as a "charger/discharger" unit. Alternatively, the discharging could be done with a separate device.

Figure 13:
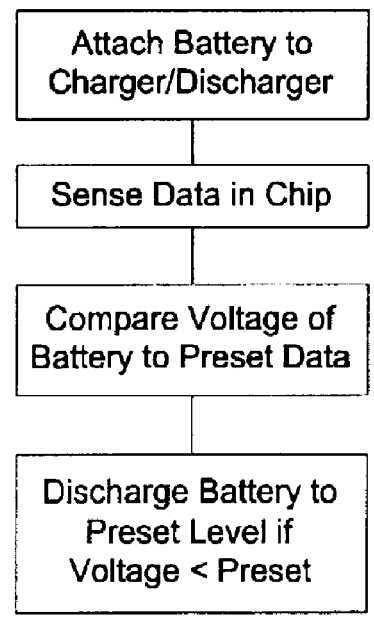
FIG. 13 is a flow chart showing the process employed by the invention.

The invention may be suitable for sterilization processes other than autoclaving. Consequently, the sterilization/charging container is intended to be permeable to all sterilization processes but impermeable to contaminants. In the preferred embodiment battery 60, 62 comprises a plurality of rechargeable Ni—Cd cells packaged with a printed circuit board having a memory chip for storing selected data. The data is read by software in charger 12 in order to control the charging/discharging cycle to which the battery is subjected. The process by which the chip interacts with the software is summarized in the flow chart of FIG. 13.

It will be understood by those skilled in the art that numerous improvements and modifications may be made to the preferred embodiment of the invention disclosed herein without departing from the spirit and scope thereof.

What is claimed is:

1. A method for providing a sterile, charged battery for use in a sterile field comprising:
   placing a battery in a sealable sterilization/charging container;
   discharging, sterilizing and charging the battery without removing it from the container; and
   removing the battery from the container into the sterile field.

2. The method according to claim 1, wherein the discharging step includes determining the voltage level of the battery prior to discharging and discharging the battery only if the voltage level is above a predetermined level.

3. The method according to claim 1, wherein the battery is sterilized in a sterilizing medium.

4. The method according to claim 3, wherein the sterilizing medium is an autoclave.

5. The method according to claim 1, wherein the container permits sterilization media to penetrate the container but does not permit contaminants to penetrate the container.

6. The method according to claim 1, wherein the discharging step includes discharging the battery to a first predetermined voltage level, and the charging step includes charging the battery to a second predetermined voltage level.

7. The method according to claim 6, wherein the battery is a nickel-cadmium battery and the first predetermined voltage level is approximately 0.9 volts per cell.

8. The method according to claim 1, further including storing the battery in a sterile state without removing it from the container.

9. A method for providing a sterile, charged battery for use in a sterile field comprising:
   providing a sealable sterilization/charging container having interior and exterior surfaces provided respectively with interior and exterior electrical terminals in electrical communication with each other;
   placing at least one rechargeable battery into the sterilization/charging container with the interior terminals contacting terminals of the battery;
   sealing the container;
   selectively discharging the battery to a predetermined voltage level;

sterilizing the battery within the container in a sterilizing medium;

providing a battery charger adapted to receive the exterior terminals of the container and charge the battery;

engaging the container with the battery charger and charging the battery to a desired voltage while it is in the sterilization/charging container; and removing the battery from the container into the sterile field.

10. The method according to claim 9, wherein the sterilizing medium is an autoclave.

11. The method according to claim 9, further comprising providing a sterilization basket for receiving the battery, the basket interposed between the battery and the interior surface and comprising an opening for providing access to the battery terminals and a handle to facilitate removing the basket and the battery from the container.

12. The method according to claim 11, wherein the sterilization/charging container and the basket are adapted to contain more than one battery.

13. The method according to claim 9, wherein the exterior terminals of the sterilization/charging container and charger terminals of the battery charger are adapted to be engaged by sliding the sterilization/charging container relative to the battery charger and disengaged by moving the container away from the charger.

14. The method according to claim 9, wherein the battery charger includes a socket adapted to receive the exterior terminals of the sterilization/charging container.

15. A method for increasing the useful life of a rechargeable battery to be sterilized for use in a sterile field comprising:

discharging the battery until its voltage reaches a predetermined discharge voltage level;

placing the battery in a container permeable to a sterilization process but impermeable to contaminants;

sterilizing the battery using the sterilization process; and charging the battery to a predetermined charge level.

16. The method according to claim 15, further comprising determining the level of charge in the battery prior to the discharging step and implementing the discharging step only if the voltage level is less than approximately 0.9 volts per cell.

17. The method according to claim 15, wherein the battery is a nickel-cadmium battery and the discharge voltage level is approximately 0.9 volts per cell.

18. The method according to claim 15, wherein the sterilization process is autoclaving.

19. A battery charging system for charging a battery, comprising:

a battery charger having at least one pair of electrical terminals, and being adapted to determine whether a voltage level of the battery is below a predetermined voltage level and, if so, depleting voltage from the battery until the predetermined voltage level is reached; and a container electrically engageable with the battery and including at least one charging terminal engageable with the pair of electrical terminals on the battery charger to enable the battery charger to charge the battery.

20. The battery charging system of claim 19, wherein the container further includes a peripheral wall, and the at least one charging terminal comprises a pair of electrical contacts attached to the peripheral wall, the electrical contacts being disposed for engagement with the pair of electrical terminals on the battery charger.

21. The battery charging system of claim 19, wherein the at least one charging terminal set includes a pair of spring loaded electrical contacts.

22. The battery charging system of claim 21, wherein the pair of spring loaded electrical contacts comprises opposed leaf springs adapted to slidably engage the pair of electrical terminals on the charging station.

23. The battery charging system of claim 19, further including a basket including at least one access aperture disposed therein and adapted to allow a battery contact set on the container to pass therethrough, the battery contact set being adapted for releasable engagement with a battery.

24. The battery charging system of claim 23, wherein the basket is perforated and includes a handle.

25. The battery charging system of claim 19, wherein the container further includes at least one battery contact set disposed in an interior of the container and comprising a pair of electrical terminals engageable with a battery, the at least one charging terminal being disposed on an exterior of the container and electrically connected to the battery contact set.

26. The battery charging system of claim 25, wherein the pair of electrical terminals on the at least one battery contact set comprises linear blades.

27. The battery charging system of claim 19, wherein the container further includes a removable cover having a plurality of apertures disposed therein.

28. The battery charging system of claim 27, further including an apertured plate removably engageable with the cover, and a membrane positioned between the cover and the apertured plate.

29. The battery charging system of claim 28, wherein the membrane is semi-permeable.

30. The battery charging system of claim 29, wherein the semi-permeable membrane is permeable to steam and heat and impermeable to contaminants.

31. A battery charging system for charging a battery to be sterilized comprising:

a sterilization/charging container for hermetically containing a battery, the container comprising a peripheral wall and at least one conductive terminal extending through the wall, the terminal comprising an inner contact component in releasable electrical contact with terminals of the battery, and an external contact component;

a battery charger/discharger for selectively discharging and charging the battery in the container, the battery charger comprising at least one battery receiving station for receiving the container, the station provided with electrical terminals for receiving the external contact component of the sterilization/charging container;

a discharge circuit means associated with the battery receiving station for determining if the level of voltage within a battery in the container at the charging station is below a predetermined level and, if so, for depleting a predetermined amount of the voltage in the battery;

interrupting means for stopping the depletion of voltage out of the battery when the predetermined amount of voltage has been depleted; and charging means associated with the battery receiving station for charging the battery within the container.

32. The battery charging system according to claim 31, wherein the electrical terminals at the battery receiving station directly contact the external contact component.

* * * * *